(12) United States Patent
Goffin et al.

(10) Patent No.: US 7,785,838 B2
(45) Date of Patent: Aug. 31, 2010

(54) VARIANTS OF MAMMALIAN PROLACTIN, PROLACTIN RECEPTOR ANTAGONISTS, AND METHODS OF USE

(75) Inventors: Vincent Goffin, Orgerus (FR); Sophie Bernichtein, Aubervilliers (FR); Paul A. Kelly, Paris (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 1349 days.

(21) Appl. No.: 10/500,968

(22) PCT Filed: Jan. 8, 2003

(86) PCT No.: PCT/EP03/00448

§ 371 (c)(1),
(2), (4) Date: May 4, 2005

(87) PCT Pub. No.: WO03/057729

PCT Pub. Date: Jul. 17, 2003

(65) Prior Publication Data

US 2006/0277614 A1     Dec. 7, 2006

(30) Foreign Application Priority Data

Jan. 8, 2002    (EP) .................. 02290030

(51) Int. Cl.
| | |
|---|---|
| *A61K 38/18* | (2006.01) |
| *C12N 15/16* | (2006.01) |
| *C12N 15/63* | (2006.01) |
| *C12N 1/21* | (2006.01) |
| *C07K 14/475* | (2006.01) |

(52) U.S. Cl. ............... 435/69.4; 435/320.1; 435/243; 435/325; 514/12; 530/399

(58) Field of Classification Search .............. None
See application file for complete search history.

(56) References Cited

U.S. PATENT DOCUMENTS 4,767,709 A * 8/1988 Nathans et al. ............. 435/363

OTHER PUBLICATIONS

Adreis (Biochem. J., 1992, vol. 281, p. 393-400).*
Goffin (J. Bio. Chem., Jul. 12, 1996, vol. 271, No. 28, 16573-16579).*
Bernichtein (Endocrine Society 82nd Annual Meeting, Toronto, Jun. 21-24, 2000, Abstract 613).*
Goffin et al. Endocrine Reviews 17(4): 385-410, 1996.*
S. Bernichteim et al.: "N-Terminal Deletion in Human Prolactin Enhances Biological Activity and Reduces Formation of Covalent Multimers" Endo 2000, Endocrine Society 82$^{nd}$ Annual Meeting, Toronto, Jun. 2000, p. 153 XP001070977, cited in the application, abstract 613, p. 153.
V. Goffin et al.: Antagonistic Properties of Human Prolactin Analogs That Show Paradoxical Agonistic Activity in the Nb2 Bioassay: J. Biol. Chem., vol. 271, No. 28, Jul. 12, 1996, pp. 16573-16579, XP002921797.
M. Llovera et al.: "Involvement of prolactin in breat cancer: redefining the molecular targets" Experimental Gerontology, vol. 35, 2000, pp. 41-51, XP002198974.
A. Tchelet et al.: "Selective Modification at the N-terminal Region of Human Growth Hormone that Shows Antagonisitc Activity" Molecular and Cellular Endocrinology, vol. 130, 1997, pp. 141-152, XP002198975.

* cited by examiner

*Primary Examiner*—Christine J Saoud
(74) *Attorney, Agent, or Firm*—Oblon, Spivak, McClelland, Maier & Neustadt, L.L.P.

(57) ABSTRACT

Mammalian prolactin (PRL) variants having a mutation or set of mutations within the 14 N-terminal amino acids that prevent the formation of a disulfide bridge between $Cys_4$ and $Cys_{11}$ and, a sterically hindering mutation or set of mutations within binding site 2 of PRL. These variants are useful as antagonists of mammalian prolactin receptors (PRLR), more particularly of human prolactin receptor (hPRLR).

9 Claims, 12 Drawing Sheets

A.

B.

A.

B.

A.

B.

A.

B.

A.

B.

| Prostate ventral lobe | Prostate dorsolateral lobe |

A.

Δ1-9G129R:  −  +                  Δ1-9G129R:  −  +

P-Erk1
P-Erk2

P-Erk1
P-Erk2

Blot: MAPK-P

Erk1
Erk2

Erk1
Erk2

Blot: MAPK

B.

SEQUENCE LISTING

```
<160> NUMBER OF SEQ ID NOS: 9

<210> SEQ ID NO 1
<211> LENGTH: 38
<212> TYPE: PRT
<213> ORGANISM: Homo sapiens
<220> FEATURE:
<221> NAME/KEY: VARIANT
<222> LOCATION: (1)..(9)
<223> OTHER INFORMATION: delta 1-9 hPRL deletion
<220> FEATURE:
<221> NAME/KEY: VARIANT
<222> LOCATION: (1)..(10)
<223> OTHER INFORMATION: delta 1-10 hPRL deletion
<220> FEATURE:
<221> NAME/KEY: VARIANT
<222> LOCATION: (1)..(12)
<223> OTHER INFORMATION: delat 1-12 hPRL deletion
<220> FEATURE:
<221> NAME/KEY: VARIANT
<222> LOCATION: (1)..(13)
<223> OTHER INFORMATION: delat 1-13 hPRL deletion
<220> FEATURE:
```

```
<221> NAME/KEY: VARIANT
<222> LOCATION: (1)..(14)
<223> OTHER INFORMATION: delat 1-14 hPRL deletion
<220> FEATURE:
<221> NAME/KEY: VARIANT
<222> LOCATION: (11)..(11)
<223> OTHER INFORMATION: delta 1-10 hPRL and delat 1-10 hPRL Cys
      replaced by Ser

<400> SEQUENCE: 1

Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
            20                  25                  30

Ser Ser Glu Met Phe Ser
        35

<210> SEQ ID NO 2
<211> LENGTH: 29
<212> TYPE: PRT
<213> ORGANISM: Homo sapiens

<400> SEQUENCE: 2

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln
            20                  25

<210> SEQ ID NO 3
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 3
ggcatatgcg atcccaggtg acccttc                                     27

<210> SEQ ID NO 4
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 4
ggcatatgtc ccaggtgacc cttcgag                                     27

<210> SEQ ID NO 5
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 5
ggcatatgca ggtgaccctt cgagacc                                     27

<210> SEQ ID NO 6
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 6
```

```
ggcatatggt gacccttcga gacctgtt                                              28

<210> SEQ ID NO 7
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 7
ggcatatgac ccttcgagac ctgtttg                                               27

<210> SEQ ID NO 8
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 8
ggcatatgct tcgagacctg tttgacc                                               27

<210> SEQ ID NO 9
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 9
ctgttacacc cacgcatgg                                                        19
```

VARIANTS OF MAMMALIAN PROLACTIN, PROLACTIN RECEPTOR ANTAGONISTS, AND METHODS OF USE

The invention relates to mammalian prolactin (PRL) variants, and their use as antagonists of mammalian prolactin receptors (PRLRs), more particularly of human prolactin receptor (hPRLR).

Prolactin is an anterior pituitary hormone involved in a wide spectrum of biological activities, among which are those related to lactation and reproduction (BOLE-FEYSOT et al., Endocr. Rev., 19, 225-268, 1998).

PRL actions on target tissues are mediated by a specific membrane-bound receptor, the Prolactin Receptor (PRLR), which belongs to the cytokine receptor superfamily (KELLY et al., Endocr. Rev., 12, 235-251, 1991).

Within the last few years, several studies demonstrated, that PRL is also synthesized in extra-pituitary sites (for review, see BEN-JONATHAN et al., Endocr. Rev., 17, 639-669, 1996), such as mammary epithelial cells (GINSBURG and VONDERHAAR, Cancer Res., 55, 2591-2595, 1995) or prostate (NEVALAINEN et al., J. Clin. Invest., 99, 618-627, 1997). In addition, it was shown that the hormone exerts a proliferative action on these cells (expressing the PRLR) via an autocrine/paracrine loop (GINSBURG and VONDERHAAR, Cancer Res., 55, 2591-2595, 1995; MERSHON et al., Endocrinology, 136, 3619-3623, 1995; CLEVENGER and PLANK, J. Mammary Gland. Biol. Neopl., 2, 59-68, 1997). Moreover, it has been suggested that the growth-promoting activity exerted by PRL on some target tissues under normal conditions may be somehow involved in promoting tumor growth under pathological conditions. Experimental evidence supporting this tumor-promoting action of PRL are i) the shortened delay of appearance of spontaneous breast tumors in PRL-transgenic mice (WENNBO et al., J. Clin. Invest., 100, 2744-2751, 1997), ii) in contrast, the delayed appearance of middle T antigen-induced breast tumors in PRL knockout mice (VOMACHKA et al., Oncogene, 19, 1077-1084, 2000), or iii) the extensive prostate hyperplasia observed in PRL-transgenic mice (WENNBO et al., Endocrinology, 138, 4410-4415, 1997).

Due to the failure of clinical treatments using dopamine agonists to reduce breast tumor progression (MANNI et al., Breast Cancer Res. Treat., 14, 289-298, 1989), PRL has been considered for a long time as a minor player in human breast cancer. However, dopamine agonists fail to target extra-pituitary PRL synthesis, which now appears at least as important as circulating, pituitary-secreted PRL in these phenomena of tumor proliferation. Developing PRLR antagonists able to compete with wild-type prolactin (WT-PRL) for receptor binding, but unable to trigger downstream signalling pathways, appears to be an alternative strategy to prevent, or at least reduce PRL-induced tumor proliferation, with potential implications in pathologies such as breast cancer and prostate hyperplasia (GOFFIN et al., Mol. Cell. Endocrinol., 151, 79-87, 1999). Although analogs of growth hormone (GH) such as G120K-hGH, were reported to antagonize the PRLR (GOFFIN et al., Endocrino., 1999), these analogs also antagonize the GH receptor (GHR). Since this duality of target may be unsuitable in a therapeutic context, development of antagonists specifically targeting the PRLR (and not the GHR) was initiated.

Formerly, the inventors have identified, localized and characterized two binding sites on the hormone, called binding sites 1 and 2, and proposed a model of PRLR activation by sequential homodimerization (GOFFIN et al., Endocr. Rev., 17, 385-410, 1996).

Based on these data, the inventors designed a first generation of human prolactin receptor (hPRLR) antagonists by introducing a sterically hindering mutation within binding site 2 of human PRL (hPRL), thereby preventing this region from docking efficiently with the PRLR molecule (GOFFIN et al., J. Biol. Chem., 271, 16573-16579, 1996). In one of these analogs, referred to as G129R-hPRL, an arginine is substituted for glycine 129 (belonging to site 2), which generates the expected steric hindrance (GOFFIN et al., J. Biol. Chem., 271, 16573-16579, 1996; GOFFIN et al., J. Biol. Chem., 269, 32598-32606, 1994).

The inventors have shown that in some bioassays this hPRL mutant is no longer able to activate the PRLR, presumably because receptor dimerization is impaired; hence, it acts as an antagonist. These properties were demonstrated first, in a bioassay involving activation of a PRL-responsive luciferase reporter gene by the human or rat PRLR (GOFFIN et al., J. Biol. Chem.; 271, 16573-16579, 1996), and second, on proliferation and activation of signalling pathways in various human breast cancer cell lines (LLOVERA et al., Oncogene, 19, 4695-4705, 2000).

However, efficient antagonistic effects required the analog being used in significant molar excess vs. WT-hPRL (10:1 to 50:1) because of its 10-fold lower affinity. In addition, in more sensitive bioassays such as the classical rat Nb2 cell proliferation bioassay, G129R-hPRL failed to exhibit any antagonistic activity (GOFFIN et al., J. Biol. Chem., 269, 32598-32606, 1994) and rather acted as a weak agonist, displaying full activity at higher concentration than hPRL. This residual agonistic activity of G129R-hPRL was confirmed by the inventors in vitro using another proliferation assay (Ba/F3 cells transfected with the hPRLR encoding plasmid), and in vivo in transgenic mice expressing G129R-hPRL analog: whereas PRLR-deficient mice are sterile and unable to develop a normal mammary gland (ORMANDY et al., Genes Dev., 11, 167-178, 1997), mice expressing G129R-hPRL analog fail to exhibit any reproductive deficiency and lactate successfully, clearly indicating that in vivo, G129R-hPRL does not abolish PRL-mediated actions.

These data clearly demonstrate that i) introducing a sterically hindering mutation within binding site 2 (G129R mutation) alters PRL biological properties, which results in antagonistic properties in some homologous (human PRLR-mediated) bioassays, ii) however, this mutation does not completely prevent receptor dimerization, since in more sensitive assays as well as in transgenic mice, the antagonistic properties are taken over by the intrinsic, residual agonistic activity of G129R-hPRL.

Thus, the latter cannot be used therapeutically as a pure antagonist of the prolactin receptor, since it may exert an effect opposite to that expected from an antagonist.

BRIEF DESCRIPTION OF THE DRAWINGS

FIG. 2A shows the binding affinity of hPRL analogs was calculated as the ratio of their $IC_{50}$ with respect to that of WT hPRL calculated from competition curves (regression in the linear part of sigmoids). Results presented in FIG. 2A are representative of at least three independent experiments performed in duplicate. FIG. 2B shows a binding assay of the G129R-containing mutants. Representative competition curves obtained with the three analogs containing the Gly129→Arg mutation are shown in FIG. 2B: WT hPRL (—●—); single mutant G129R-hPRL (—◆—); double mutant Δ1-9-G129R-hPRL (—■—); double mutant Δ1-14-G129R-hPRL (—▲—). The three curves are displaced to the right by ~1 order of magnitude compared to WT hPRL, reflecting 10 fold lower affinity for the receptor. Averaged from three independent experiments, $IC_{50}$ were 166±47 ng/ml for Δ1-9-G129R and 187±49 ng/ml for Δ1-14-G129R, compared to 18±5 ng/ml (for WT hPRL). None of the N-terminal deletion improves affinity compared to G129R-hPRL (single mutant).

FIG. 3A shows cell proliferation in presence of increasing concentrations of hPRL (—●—), Δ1-9-hPRL (—□—) and Δ1-14-hPRL (—Δ—); FIG. 3B shows cell proliferation in presence of increasing concentrations of hPRL (—●—), Δ1-10-hPRL (——*——), Δ1-11-hPRL (——○——), Δ1-12-hPRL (——□——), Δ1-13-hPRL (——◇——).

FIG. 4A shows proliferation of Ba/F3 cells in presence of increasing concentrations of hPRL (—●—), Δ1-9-hPRL (—□—) and Δ1-14-hPRL (—Δ—); FIG. 4B shows proliferation of Ba/F3 cells in presence of increasing concentrations of hPRL (—●—), Δ1-10-hPRL (——*——), Δ1-11-hPRL (——603——), Δ1-12-hPRL (——□——), Δ1-13-hPRL (——◇——).

FIG. 8A shows agonism by cell proliferation in presence of increasing concentrations of purified WT hPRL (■), G129R-hPRL (▤), Δ1-9-G129R-hPRL (≡), and Δ1-14-G129R-hPRL (▤). Maximal effect of WT hPRL is obtained at 10 ng/ml. G129R-hPRL induced sub-maximal proliferation with a dose-response curve displaced by 2 logs to the high concentrations. In contrast, none of the double mutants (Δ1-9-G129R-hPRL and Δ1-14-G129R-hPRL) induced significant proliferation. As in the Nb2 assay, the curve obtained for G129R-hPRL was displaced to the right by ~2 log units and achieved sub-maximal (50-80%) level compared to hPRL. At high concentrations, hPRL and G129R-hPRL displayed bell-shaped curves, a typical observation when using these ligands (KI-NET et al., Recent Res. Devel. Endocrinol., 2, 1-24, 2001). Both Δ1-9-G129R-hPRL and Δ1-14-G129R-hPRL failed to display any agonistic activity, even at concentration as high as 10 μg/ml. Antagonistic assays were performed by competing a fixed concentration of WT hPRL (10 ng/ml) with increasing concentrations of the analogs. FIG. 8B shows cell proliferation in presence of increasing concentrations of Δ1-9-G129R-hPRL (—■—), Δ1-14-G129R-hPRL (—▲—), G129R-hPRL (—◆—) competing with the fixed concentration of WT hPRL.

Bottom panel (MAPK): total MAPK in the same samples. B: densitometric quantification of anti-phosphorylated MAPK blot (top panels).

The inventors have undertaken to develop more efficient hPRLR antagonists. They have previously studied the potential involvement of the N-terminal tail of hPRL in its binding to the PRLR. They have engineered iterative N-terminal deletions in hPRL, ranging from removal of the 9 first residues up to the 14 first résidues; the N-terminal sequences of wild type hPRL and hGH and of the deletion mutants of hPRL are shown on FIG. 1.

Figure 1:
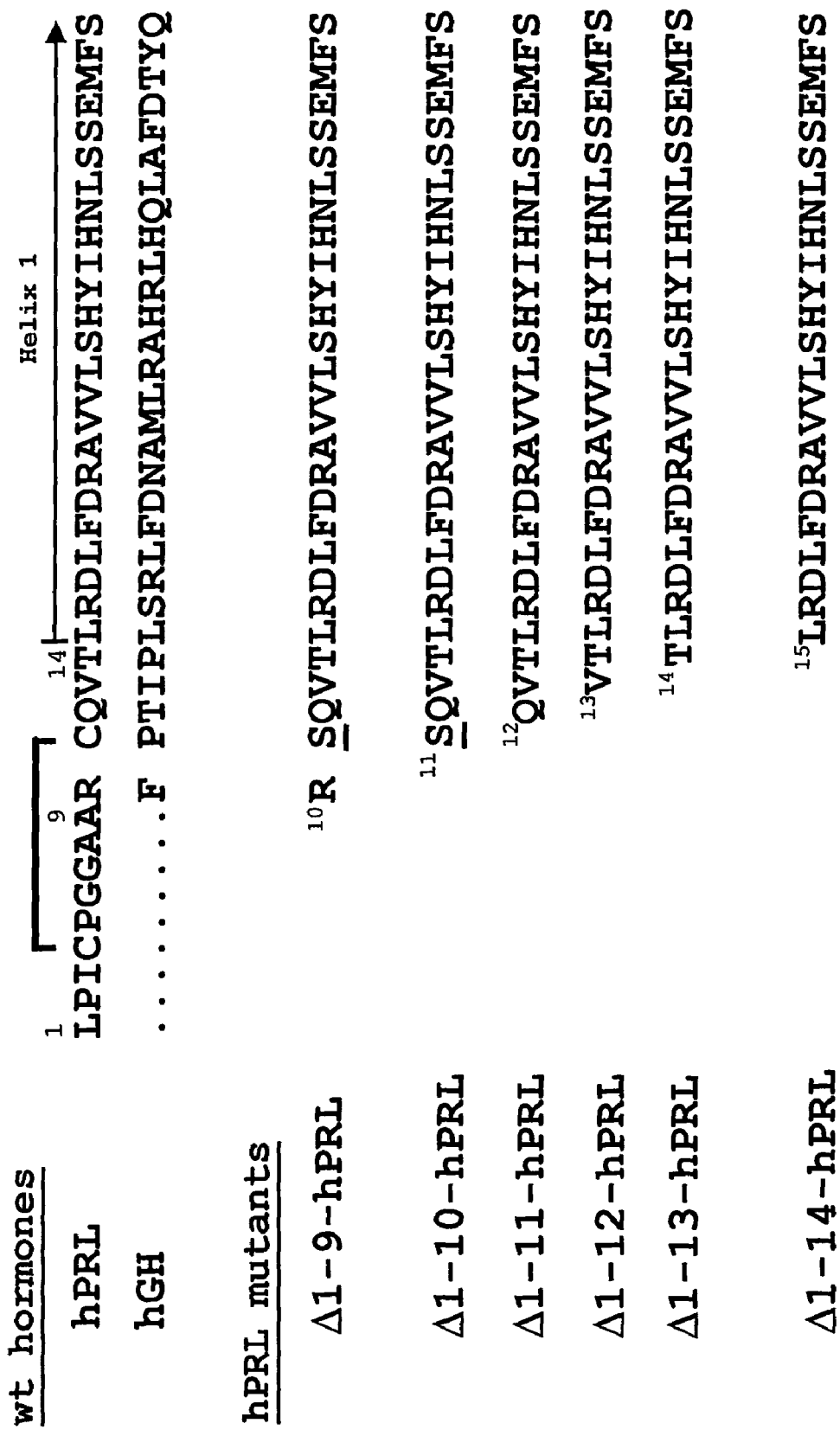
FIG. 1 shows the N-terminal sequences of wild type hPRL and hGH and of the deletion mutants of hPRL are shown on FIG. 1. Legend of FIG. 1: Top: PRL (SEQ ID NO: 1) and GH (SEQ ID NO: 2) N-terminal sequences are aligned; the N-terminus is 9 residues longer in PRL, including a disulfide bond between $Cys_4$ and $Cys_{11}$. An arrow identifies putative helix 1 as predicted by homology modeling. Bottom: incremental deletions of hPRL N-terminus. Deletion of the 9 first residues (Δ1-9-hPRL) mimics N-terminus of hGH, whereas deletion of the 14 first residues (Δ1-14-hPRL) removes the N-terminus tail in its entirety.

Legend of FIG. 1:

Top: PRL (SEQ ID No:1) and GH (SEQ ID No:2) N-terminal sequences are aligned; the N-terminus is 9 residues longer in PRL, including a disulfide bond between $Cys_4$ and $Cys_{11}$. An arrow identifies putative helix 1 as predicted by homology modeling.

Bottom: incremental deletions of hPRL N-terminus. Deletion of the 9 first residues (Δ1-9-hPRL) mimics N-terminus of hGH, whereas deletion of the 14 first residues (Δ1-14-hPRL) removes the N-terminus tail in its entirety.

They observed that deletion of the 9 first residues of hPRL (Δ1-9-hPRL) slightly enhanced the affinity for the PRLR leading to increased maximal activity compared to wild-type hPRL (WT hPRL) in the luciferase assay, while deletion of the 14 first residues (Δ1-14-hPRL) results in a decrease of the affinity and maximal activity (Endocrine Society 82$^{nd}$ Annual Meeting, Toronto, Jun. 21-24 2000, Abstract 613).

The inventors have now undertaken to test the effect of N-terminal deletions on the affinity and antagonistic activity of the G129R-hPRL analog. Therefore, they engineered two N-terminal deletions in G129R-hPRL, by removal of the 9 first residues (mutant Δ1-9-hPRL) and of the 14 first residues (mutant Δ1-14-hPRL).

The inventors found that, unexpectedly, both mutations completely abolished the residual agonist activity of G129R-hPRL.

Without being limited by theory, it may be supposed that these N-terminal deletions impair the formation of the disulfide bridge between $Cys_4$ and $Cys_{11}$, and that other mutations preventing the formation of said disulfide bridge may also have advantageous effect on reducing the residual agonist activity.

Accordingly, the present invention provides an antagonist of a mammalian prolactin receptor, wherein said antagonist is a variant of mammalian prolactin having the following mutations:

a) a mutation or set of mutations within the 14 N-terminal amino acids, wherein said mutation or set of mutations prevents the formation of the disulfide bridge between $Cys_4$ and $Cys_{11}$, and b) a sterically hindering mutation or set of mutations within binding site 2 of prolactin.

Mutation(s) a) impairing the formation of the $Cys_4$-$Cys_{11}$ disulfide bridge comprise for instance: deletions including $Cys_4$ and/or $Cys_{11}$, or substitution of $Cys_4$ and/or $Cys_{11}$ by an amino acid other than a cystein.

Mutation(s) b) comprise in particular any substitution of a small amino acid within binding site 2 of PRL by a large and/or charged amino acid in order to introduce a steric hindrance. Examples of such mutations are for instance substitution of at least one residue among $Gln_{122}$, $Leu_{125}$, $Ser_{26}$, $Ala_{22}$ or $Gly_{129}$, preferably $Ala_{22}$, more preferably $Gly_{129}$, by residues such as Tyr, Phe, Asp, Glu, Arg, Lys or Trp, preferably Arg, Lys or Trp.

According to a preferred embodiment of the invention, mutation(s) a) comprises the deletion of at least the 4 N-terminal residues, preferably of at least the 9 N-terminal residues of PRL.

In cases wherein the N-terminal deletion is shorter than 11 amino acids, mutation(s) a) may further comprise the substitution of the $Cys_{11}$ residue by an amino acid other than a cystein. This further allows an easier purification of the variants, by avoiding aggregation thereof that may result from the presence of free SH groups.

Preferred PRL variants of the invention are variants comprising the following mutations:

a deletion of at least the 9 N-terminal residues and up to the 14 N-terminal residues; and a G129R substitution.

Advantageously, the variants of the invention are variants of human prolactin (hPRL).

The present invention also provides polynucleotides encoding the PRL variants of the invention.

Polynucleotides of the invention may be obtained by the well-known methods of recombinant DNA technology and/or of chemical DNA synthesis. These methods also allow to introduce the desired mutations in a naturally occurring DNA sequence.

The invention also provides recombinant DNA constructs comprising a polynucleotide of the invention, such as expression cassettes wherein said polynucleotide is linked to appropriate control sequences allowing the regulation of its transcription and translation in a host cell, and recombinant vectors comprising a polynucleotide or an expression cassette of the invention.

These recombinant DNA constructs can be obtained and introduced in host cells by the well-known techniques of recombinant DNA and genetic engineering.

The invention also comprises a prokaryotic or eukaryotic host cell transformed by a polynucleotide encoding a PRL variant of the invention.

A PRL variant of the invention can be obtained by culturing a host cell containing an expression vector comprising a nucleic acid sequence encoding said PRL variant, under conditions suitable for the expression thereof, and recovering said variant from the host cell culture.

The invention also provides transgenic non-human animals, in particular transgenic non-human mammals, transformed with a polynucleotide encoding a PRL variant of the invention. Suitable methods for the preparation of transgenic animals are for instance disclosed in: *Manipulating the Mouse Embryo*, 2$^{nd}$ Ed., by HOGAN et al., Cold Spring Harbor Laboratory Press, 1994; *Transgenic Animal Technology*, edited by C. PINKERT, Academic Press Inc., 1994; *Gene Targeting: A Practical Approach*, edited by A. L. JOYNER, Oxford University Press, 1995; *Strategies in Transgenic Animal Science*, edited y G. M. MONASTERSKY and J. M. ROBL, ASM Press, 1995; *Mouse Genetics: Concepts and Applications*, by Lee M. SILVER, Oxford University Press, 1995.

The invention also relates to a therapeutic composition comprising a PRL variant of the invention, or a polynucleotide encoding said PRL variant, optionally mixed with suitable carriers and/or excipient(s).

For instance, the PRL variants of the invention can further be conjugated to one or more chemical groups, in order to increase their molecular weight. Examples of suitable chemical groups include polyols, such as polyethylene glycol (PEG) or heterologous polypeptides preferably hydrosoluble polypeptides, such as serum albumin of fragments thereof.

Therapeutic compositions of the invention are useful as PRLR antagonists, in particular for treating or preventing diseases involving PRLR-mediated effects, such as tumoral proliferation involving any form of benign or malignant tumor (hyperplasia, dysplasia, neoplasia, adenoma, carcinoma) in any PRL target tissue (breast, prostate, liver, pituitary, lymphocytes), auto-immune diseases (lupus erythematosus, rheumatoid arthritis), hyperprolactinemia, typically, any diseases arising from an overstimulation of the PRLR (hypermastia, reproduction disorders) (BOLE-FEYSOT et al., Endocr. Rev., 1998).

The therapeutic compositions of the invention can be administered in various ways:

They can be used systemically or locally. A preferred route of administration is the parenteral route, including for instance intramuscular, subcutaneous, intravenous, intraperitoneal, or local intratumoral injections.

The oral route can also be used, provided that the composition is in a form suitable for oral administration, able to protect the active principle from the gastric and intestinal enzymes.

In the case wherein the therapeutic composition includes a polynucleotide encoding a PRL variant of the Invention, said nucleotide is generally inserted in an expression cassette allowing its expression in a target organ or tissue.

The expression cassette can be directly transferred in the cells as naked DNA, or placed in an appropriate vector, such as a viral vector, for instance an adenovirus derived vector.

Gene transfer can be performed ex vivo on cells removed from the subject to be treated and thereafter re-implanted into said subject, or can be performed by direct administration of the nucleic acid to said subject.

The choice of the method of transfer and/or of the vector depends on the target organ or tissue, and/or on whether a short-time expression (transient expression) or a more stable expression is wanted.

Since the PRL variants of the Invention have a lower affinity for the PRL receptor than native PRL, the amount administered will be chosen in order to supply a large excess of PRL variant over endogenous PRL in the blood and/or target tissue. On the other hand, due to the lack of residual agonist activity of PRL variants of the invention, high doses thereof can be administered, without risk of unwanted agonist effects. In most of cases, an amount of PRL variant resulting in a 10 to 100-fold excess over endogenous PRL will be suitable. If necessary, an amount of PRL variant resulting in a 1000-fold excess or more over endogenous can be administered.

The present invention will be further illustrated by the following additional description, which refers to examples illustrating the properties of hPRL antagonists of the invention. It should be understood however that these examples are given only by way of illustration of the invention and do not constitute in any way a limitation thereof.

EXAMPLE 1

Production and Purification of hPRL Analogs

Hormones

All PRL (wild-type and mutant forms) used in this study were produced by recombinant technology: WT hPRL, the binding site 2 analog G129R-hPRL (Gly 129 replaced with Arg), single N-terminal deleted mutants (Δ1-9-hPRL, Δ1-10-hPRL, Δ1-11-hPRL, Δ1-12-hPRL, Δ1-13-hPRL, Δ1-14-hPRL), the double mutants in which mutation G129R was introduced into Δ1-9-hPRL or Δ1-14-hPRL (generating Δ1-9-G129R-hPRL and Δ1-14-G129R-PRL analogs).

Construction of Mutated hPRL Expression Vectors

N-Terminal Deletions

Constructions

Construction of expression plasmids encoding Δ1-9-hPRL, Δ1-10-hPRL, Δ1-11-hPRL, Δ1-12-hPRL, Δ1-13-hPRL and Δ1-14-hPRL analogs was performed using Polymerase Chain Reaction (PCR); plasmid pT7L-hPRL (PARIS et al., Biotechnol. Appl. Biochem., 12, 436-449, 1990) was used as template. Sequences of 5' primers correspond to the 5' sequence of the hPRL cDNA lacking the 9 (Δ1-9-hPRL) up to 14 (Δ1-14-hPRL) N-terminal codons. A unique NdeI restriction site (CATATG) containing the ATG codon (methionine initiator) was inserted in the 5' primer. TGC codon encoding Cys 11 was mutated into TCC encoding a serine.

The sequence of 5' primers are the following (5' to 3'):

Δ1-9    (SEQ ID No:3): GGCAT<u>ATG</u>CGATCCCAGGTGACCCTTCG

Δ1-10   (SEQ ID No:4): GGCAT<u>ATG</u>TCCCAGGTGACCCTTCGAG

Δ1-11   (SEQ ID No:5): GGCAT<u>ATG</u>CAGGTGACCCTTCGAGACC

-continued

Δ1-12   (SEQ ID No:6): GGCAT<u>ATG</u>GTGACCCTTCGAGACCTGTT

Δ1-13   (SEQ ID No:7): GGCAT<u>ATG</u>ACCCTTCGAGACCTGTTTG

Δ1-14   (SEQ ID No:8): GGCAT<u>ATG</u>CTTCGAGACCTGTTTGACC

The 3' primer is identical for all analogs; it corresponds to a sequence in the non-coding region of the hPRL cDNA, located in 3' of the unique HindIII restriction site (SEQ ID No:9): 5'CTGTTACACCCACGCATGG3'.

The PCR reaction was performed as follows: 200 μM dNTP; 45 μM MgCl$_2$, 1.5 μl Taq Polymerase (5 u/μl), PCR buffer, 10 ng of template (plasmid pT7L-hPRL), 20 pmoles of each primers. PCR was performed for 25 cycles: 94° C. (30 sec), 56° C. (30 sec), 72° C. (1 min). PCR products were subcloned into TA cloning vector (pCR II.1), then recombinant TA plasmids were digested using NdeI and HindIII and purified inserts were ligated into pT7L plasmid linearized using identical restriction enzymes. After transformation, E. coli BL21(DE3) colonies were analysed for their DNA content; plasmids were extracted and digested to confirm the presence of expected inserts, then sequenced to check the expected mutations.

Production and Purification of Proteins

Recombinant WT hPRL and hPRL analogs were overexpressed in a 1 liter culture of E. coli BL21(DE3) and purified as previously described (PARIS et al., Biotechnol. Appl. Biochem., 12, 436-449, 1990; GOFFIN et al., Mol. Endocrinol., 6, 1381-1392, 1992). Briefly, when the OD$_{600}$ of bacterial cultures reached ~0.9, overexpression was induced using 2 mM isopropylthiolgalactoside (IPTG) for 4 h (OD$_{600}$ ~2.5 after 4 h). Cell lysis was performed using a cell disintegrator (Basic Z, Cell D, Roquemaure, France). Proteins were overexpressed as insoluble inclusion bodies that were solubilized in 8 M urea (5 min at 55° C., then 2 h at room temperature) and refolded by continuous dialysis (72 h, 4° C.) against 50 mM NH$_4$HCO$_3$, pH 8.

Protein purification was performed using chromatography equipment (GRADIFRAC) and columns (HITRAP Q SEPHAROSE, SEPHACRYL S200 High Resolution) purchased from AMERSHAM-PHARMACIA BIOTECH (Orsay, France).

Two alternative protocols were used. The dialyzed proteins were centrifuged for at least 60 minutes (9000×g) to remove aggregates before loading the cleared supernatant mixture onto an anion exchange HITRAP Q column (equilibrated in 50 mM NH$_4$HCO$_3$, pH 8) PRLs eluted in two peaks, one major peak eluted at a concentration of 150 mM NaCl, and a minor one eluted at a higher salt concentration (~200 mM). Analytical gel filtration of these fractions indicated that the major peak corresponds to monomeric PRL, whereas the minor one includes various multimeric forms. Alternatively, refolded (dialyzed) proteins were concentrated by tangential flow ultrafiltration using a YM10 MINIPLATE bioconcentrator (MILLIPORE CORP.-AMICON, Bedford, Mass.; 500 ml/min flow rate), then the concentrated solution was centrifuged (10 min, 9000×g) to remove aggregates formed upon ultrafiltration. Supernatants were purified by gel filtration chromatography using a high resolution SEPHACRYL S-200 column equilibrated in 50 mM NH$_4$HCO$_3$, 150 mM NaCl, pH 8. This second protocol usually led to lower yields due to higher protein precipitation upon the ultrafiltration step. Fractions corresponding to monomeric hPRLs (eluted from molecular sieve or anion exchange columns) were pooled, quantified, aliquoted and stored at −20° C.

Protein size and purity were assessed using 15% SDS-PAGE under reducing (beta-mercaptoethanol) or non-reducing conditions. Protein fractions were quantified by Bradford protein assay (BIO-RAD Laboratories, Inc., Ivry-sur-Seine, France), using BSA as the reference.

Double Mutants

Expression plasmids encoding analogs Δ1-9-G129R-hPRL and Δ1-14-G129R-hPRL were constructed by substituting the EcoRI-BglII fragment from pT7L-G129R-hPRL plasmid (containing the G129R mutation) (GOFFIN et al., J. Biol. Chem., 269, 32598-32606, 1994) for the corresponding EcoRI-BglII fragment in pT7L-Δ1-9-hPRL and pT7L-Δ1-14-hPRL expression vectors. Clones obtained were analysed for the presence of the insert, then sequenced to check the expected mutations. Analog expression using BL21(DE3) bacteria, and protein purification were performed as described above.

All hPRL mutants produced in bacteria as inclusion bodies refolded correctly, suggesting that the various mutations do not disturb global conformation of the protein. This was confirmed by analysis of their content in secondary structure, performed by circular dichroism (not shown). The only repeated difference between mutated and WT hPRL was that N-terminal deletions tended to increase the monomeric/multimeric ratio observed after protein refolding. It is believed that removal of the two N-terminus cysteines (Cys4-Cys11) prevents formation of covalent multimers responsible for intermolecular disulfide bonding between these residues.

EXAMPLE 2

Affinity of HPRL Analogs for Human PRLR

Binding Studies

The affinity of the various hPRL analogs for the human PRLR was estimated by their ability to compete $[^{125}I]$-hPRL for binding to this receptor. Binding affinities were determined using cell homogenates of HL5 cells (expressing the human PRLR), following the procedure previously described (KINET et al., J. Biol. Chem., 274, 26033-26043, 1999).

Briefly, hPRL was iodinated using IODOGEN, and its specific activity was in the range of 40-50 µCi/µg. Binding assays were performed overnight at room temperature using 150-300 µg cell homogenate protein in the presence of 30,000 cpm $[^{125}I]$-hPRL and increasing concentrations of unlabeled competitor (WT or mutated hPRL).

The affinity of WT hPRL for the human PRLR (using HL5 cell homogenates) as calculated by Scatchard analysis indicated a Kd of $3.4 (\pm 1.3) \times 10^{-10}$ M (KINET et al., J. Biol. Chem., 1999).

Binding Assay of Single N-Terminal hPRL Mutants.

The relative binding affinity of hPRL analogs was calculated as the ratio of their $IC_{50}$ with respect to that of WT hPRL calculated from competition curves (regression in the linear part of sigmoids). Results presented in FIG. 2A are representative of at least three independent experiments performed in duplicate.

These results show that while deletion of the 10, 11, 12 or 13 first residues does not affect hPRL affinity for its receptor (competition curves superimposed), the curve obtained with Δ1-9-hPRL was slightly displaced to the left compared to WT hPRL, representing a small increase of 20% in affinity, whereas that of Δ1-14-hPRL was displaced to the right, reflecting 2 to 3 fold lower affinity (40% relative affinity).

Binding Assay of the G129R-Containing Mutants.

Figure 2:
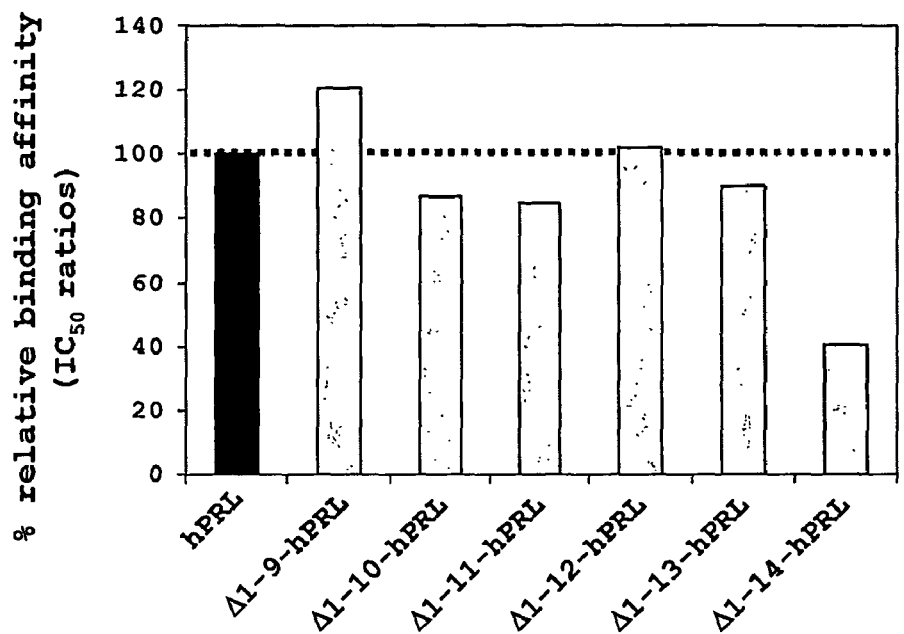
FIG. 2A and 2B depict the binding affinities of N-terminal and G129R-containing hPRL analogs.
Figure 2:
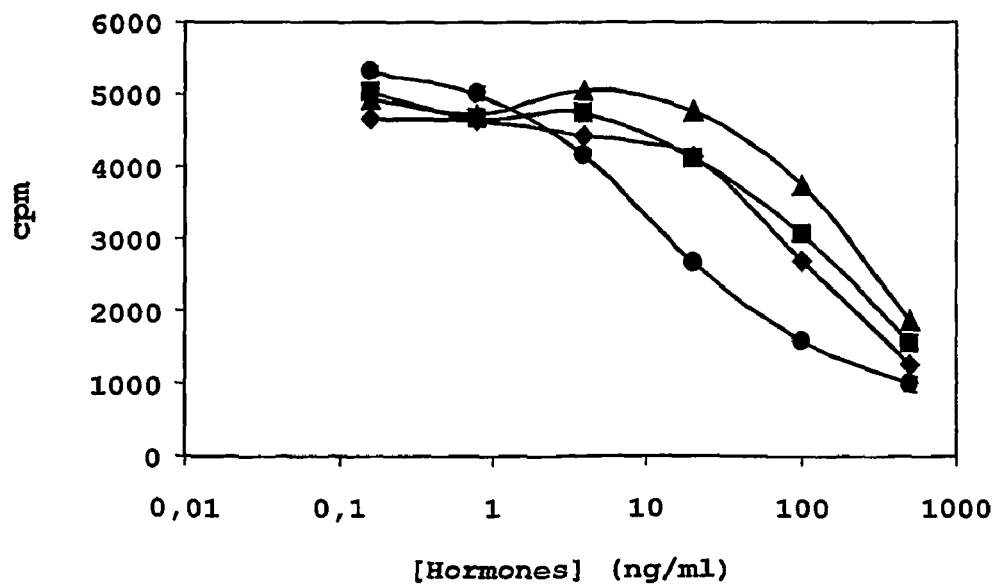

Representative competition curves obtained with the three analogs containing the Gly129→Arg mutation are shown in FIG. 2B: WT hPRL (—●—); single mutant G129R-hPRL (—◆—); double mutant Δ1-9-G129R-hPRL (—■—); double mutant Δ1-14-G129R-hPRL (—▲—).

The three curves are displaced to the right by ~1 order of magnitude compared to WT hPRL, reflecting 10 fold lower affinity for the receptor. Averaged from three independent experiments, $IC_{50}$ were 166±47 ng/ml for Δ1-9-G129R and 187±49 ng/ml for Δ1-14-G129R, compared to 18±5 ng/ml (for WT hPRL). None of the N-terminal deletion improves affinity compared to G129R-hPRL (single mutant).

EXAMPLE 3

Bioactivity of HPRL Analogs

Experimental Protocols

Nb2 Cell Proliferation Assay

The reference bioassay for lactogenic hormones is the lactogen-induced proliferation of rat Nb2 lymphoma cells. Rat Nb2 lymphoma cells were obtained from P. W. GOUT (Vancouver, Canada) and cultured as previously described (BERNICHTEIN et al., Endocrinology, 142, 3950-3963, 2001). Nb2 cells were routinely maintained in RPMI 1640 supplemented with 10% HS, 10% heat-inactivated FCS, 2 mM glutamine, 50 U/ml penicillin, 50 µg/ml streptomycin, and 100 mM β-mercaptoethanol. The proliferation assay was performed as initially described (TANAKA et al., J. Clin. Endocrinol. Metab., 51, 1058-1063, 1980) with minor modifications (BERNICHTEIN et al., Endocrinology, 142, 3950-3963, 2001). Briefly, the assay was performed in 96-well plates using $2 \times 10^4$ cells/well on starting day, in a final volume of 200 µl, including hormones. Cell proliferation was estimated after 3 days of hormonal stimulation by adding 10 µl WST-1 tetrazolium salt (ROCHE, Meylan, France). This survival reagent is metabolized by mitochondria of living cells, which leads to an increase in the OD measured at 450 nm ($OD_{450}$) in a manner that is proportional to the number of cells counted by hemocytometer (BERNICHTEIN et al., Endocrinology, 142, 3950-3963, 2001). The experiments were performed at least three times in triplicate or quadruplicate.

Human PRLR Transcriptional Bioassay (HL5)

Clone HL5 are 293 HEK fibroblasts stably transfected with plasmids encoding the human PRLR and a PRL-responsive reporter gene (containing the sequence encoding the luciferase gene under the control of a six-repeat sequence of the lactogenic hormone response element (LHRE) which is the DNA-binding element of STAT5 (KINET et al., J. Biol. Chem., 274, 26033-26043, 1999).

The HL5 clone was routinely cultured in DMEM-Nut F12 medium supplemented with 10% FCS, 2 mM glutamine, 50 U/ml penicillin, 50 µg/ml streptomycin, and 700 µg/ml G-418 (clonal selection). The assay was performed in 96-well plates using $5 \times 10^4$ cells/100 µl/well in medium containing only 0.5% FCS. Cells were allowed to adhere overnight, then 100 µl hormones diluted in FCS-free medium were added to each well. After 24 h of stimulation, cells were lysed (50 µl lysis buffer), then luciferase activity contained in 15 µl cell lysate was counted for 10 sec (BERNICHTEIN et al., Endocrinology, 142, 3950-3963, 2001; KINET et al., J. Biol. Chem., 274, 26033-26043, 1999). To avoid inter-assay variations, all analogs to be compared were systematically tested in the same experiment. In agonism experiments 100 µl of [2x] hormones ("2×"=concentrated 2 times compared to the final concentration required) to be tested are added, whereas in antagonism experiments, a mix of 50 µl of [4×] hormone analogs combined with 50 µl of [4×] WT hPRL (to obtain a final concentration of 1 µg/ml) were added.

Ba/F3-hPRLR Cell Proliferation Bioassay

Ba/F3 cells are mouse pro-B lymphoid cells dependent on Interleukin-3 (IL-3) for growth. Ba/F3-hPRLR cells were obtained after transfection using a plasmid encoding the hPRLR, and a double selection involving G-418 treatment and substitution of hPRL for IL-3 in the growth medium. Cells were transfected (electroporation) using the plasmid encoding the hPRLR and the population stably expressing the receptor was selected after G-418 treatment. Ba/F3-hPRLR cells were maintained in RPMI 1640 medium supplemented with 10% heat-inactivated FCS, 2 mM glutamine, 50 U/ml penicillin, 50 µg/ml streptomycin, 500-1000 µg/ml G-418, and 10 ng/ml WT-hPRL instead of IL-3. Optimal conditions of bioassay (cell number, starvation time and medium, etc) were determined using WT hPRL as ligand, and are the following: before the proliferation assay, cells were starved for 6 hours in 1% FCS RPMI medium (with additives), then distributed in 96 well-plates at a density of $5 \times 10^4$ cells/well in a final volume of 100 µl in the same medium (excluding hormones). In agonism experiments, 100 µl of [2×] hormones were added; in antagonism experiments, 50 µl of [4×] hormones to be tested for antagonistic properties and 50 µl of [4×] WT hPRL (final concentration of 10 ng/ml) were added. Cell proliferation was monitored after 3 days of hormonal stimulation using 10 µl of WST-1. Experiments were performed at least three times in triplicate or quadruplicate.

Results

N-Terminal Deleted Analogs

Agonism

Nb2 Cell Proliferation Assay

According to previous reports, monomeric hPRL induces cell proliferation in the classical Nb2 cell proliferation assay with a maximal effect at 1-2 ng/ml.

Figure 3:
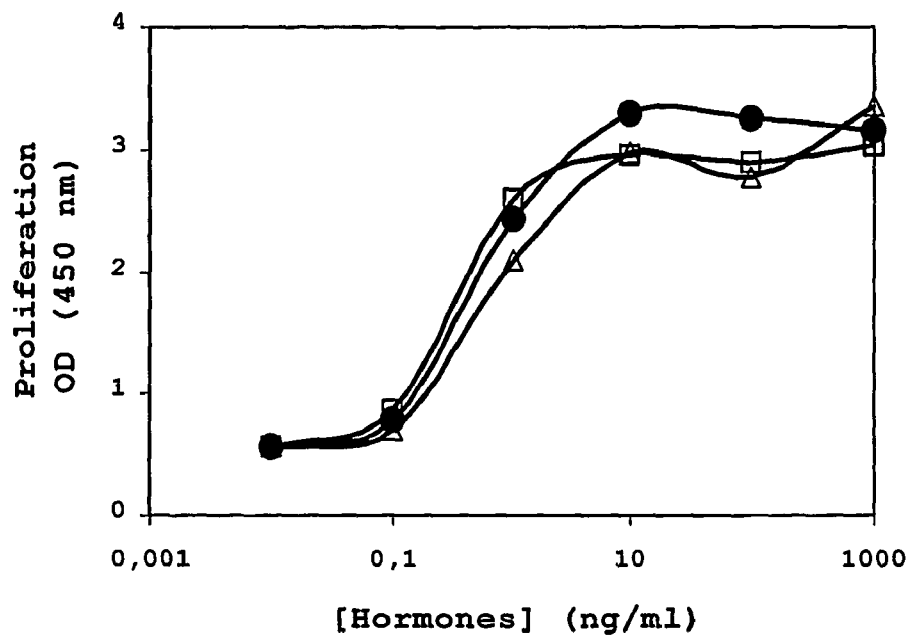
FIG. 3 shows agonism of N-terminal deleted analogs using the Nb2 cell proliferation assay.
Figure 3:
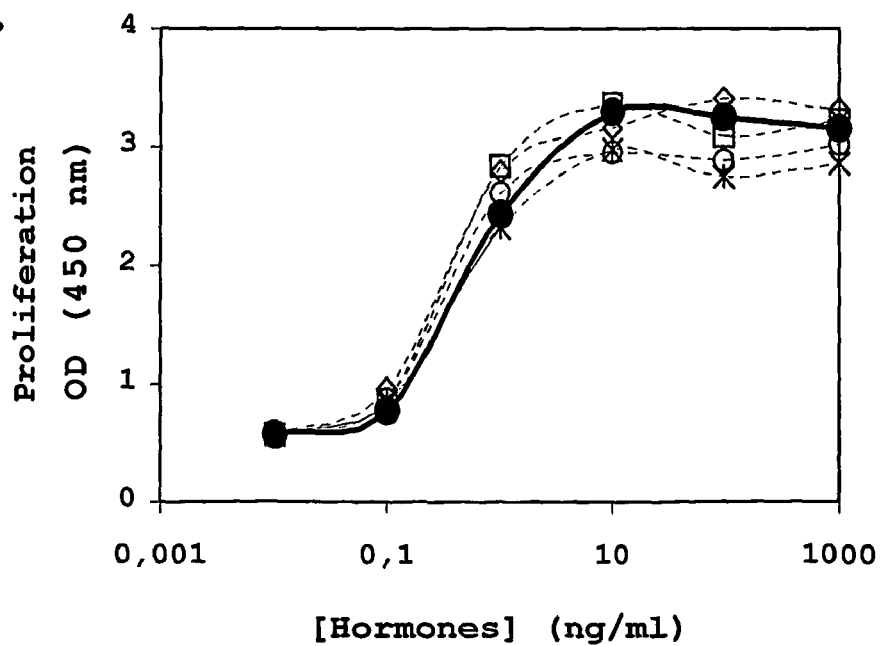

FIG. 3A shows cell proliferation in presence of increasing concentrations of hPRL (—●—), Δ1-9-hPRL (—□—) and Δ1-14-hPRL (—Δ—); FIG. 3B shows cell proliferation in presence of increasing concentrations of hPRL (—●—), Δ1-10-hPRL (—*—), Δ1-11-hPRL (—○—), Δ1-12-hPRL (—□—), Δ1-13-hPRL (—◇—).

Dose-response curves for this assay were similar for all mutants (Δ1-9-hPRL→Δ1-14-hPRL) and WT hPRL ($EC_{50}$ ranging from 0.57 to 0.87 ng/ml), indicating that N-terminal deletions do not dramatically alter the mitogenic activity of hPRL in this assay.

Ba/F3-hPRLR Cell Proliferation Bioassay

In contrast to the assay with Nb2 cells, the hPRLR-mediated proliferation assay with Ba/F3 cells displayed different mitogenic activities of the analogs. WT hPRL induced growth of this cell population in a dose-dependent manner, with maximal effect at ~10 ng/ml, which correlates with the cell selection by substituting 10 ng/ml hPRL for IL-3 in routine culture medium.

Figure 4:
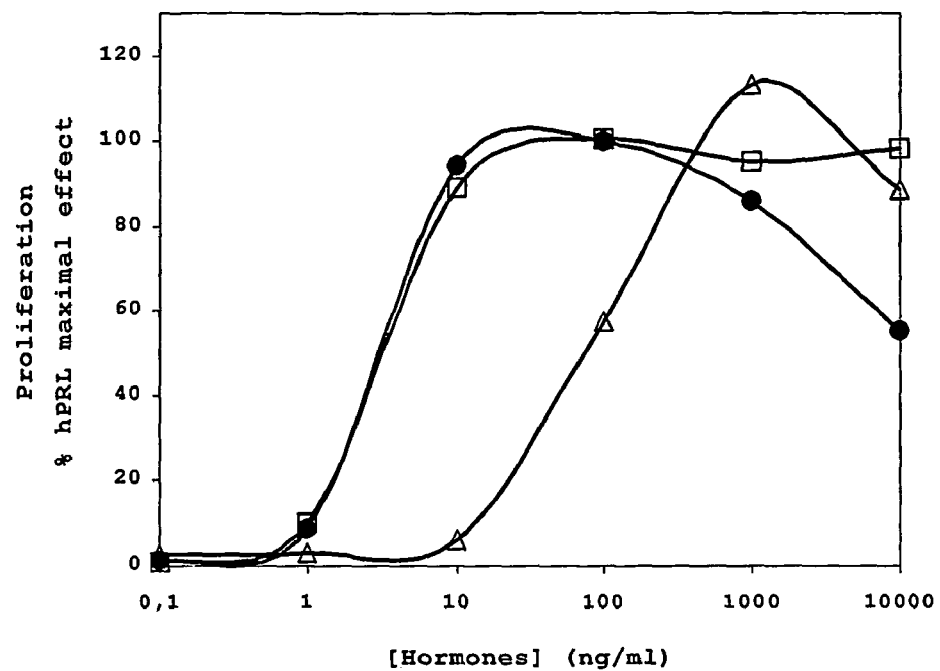
FIG. 4 shows the different mitogenic activities of analogs by the Ba/F3-hPRLR cell proliferation bioassay.
Figure 4:
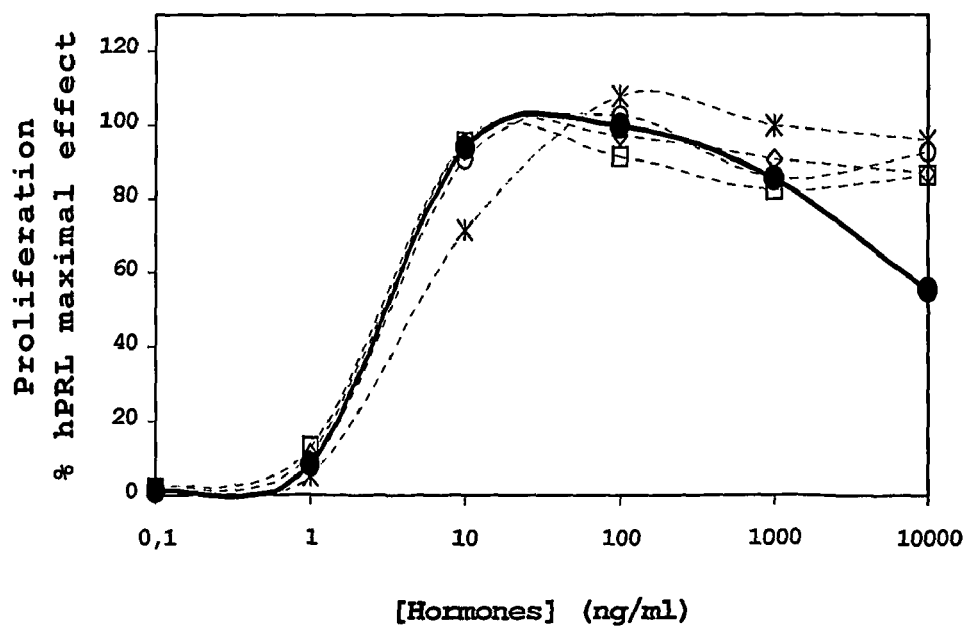

FIG. 4A shows proliferation of Ba/F3 cells in presence of increasing concentrations of hPRL (—●—), Δ1-9-hPRL (—□—) and Δ1-14-hPRL (—Δ—); FIG. 4B shows proliferation of Ba/F3 cells in presence of increasing concentrations of hPRL (—●—), Δ1-10-hPRL (—*—), Δ1-11-hPRL (—○—), Δ1-12-hPRL (—□—), Δ1-13-hPRL (—◇—).

The dose-response curves obtained with analogs Δ1-9-hPRL, Δ1-10-hPRL, Δ1-11-hPRL, Δ1-12-hPRL and Δ1-13-hPRL were superimposed to that obtained with hPRL, reflecting no alteration of bioactivity. In contrast, the curve of Δ1-14-hPRL was displaced to the right by >1 log, reflecting significantly altered ability to activate the hPRLR in this assay. All analogs were able to induce a maximal level of cell division provided sufficient hormone concentrations were added in the assay.

Human PRLR Transcriptional Bioassay (HL5)

Figure 5:
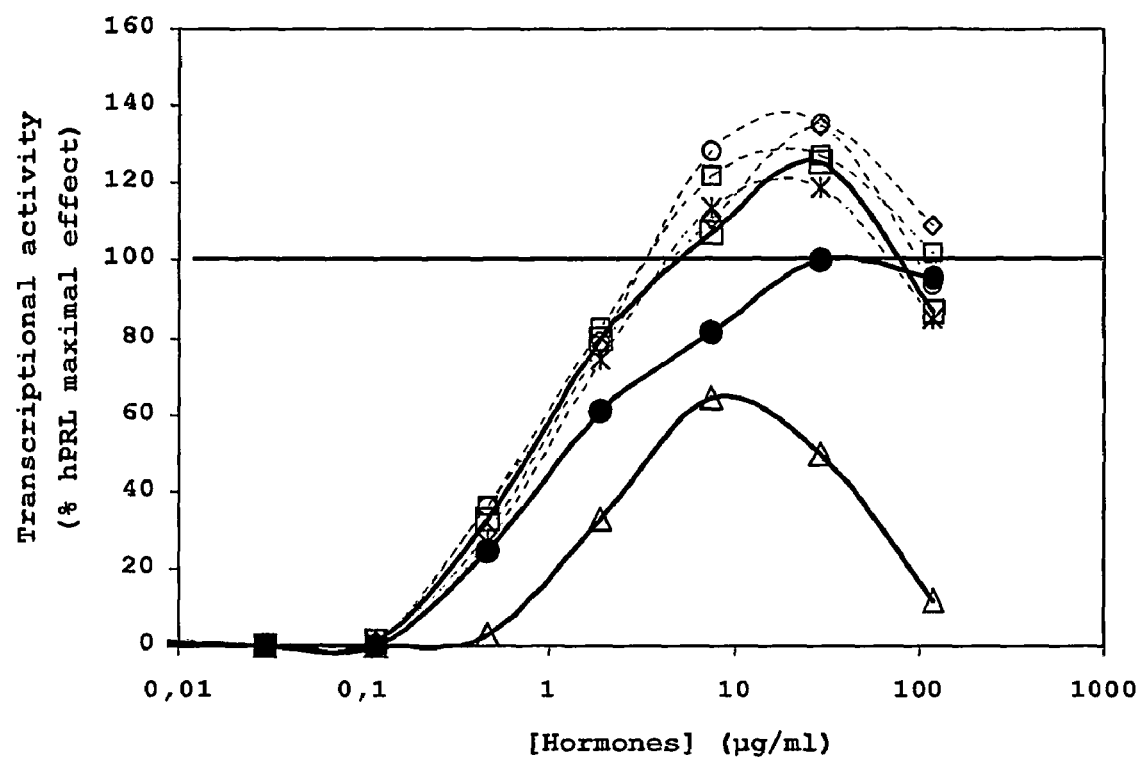
FIG. 5 provides data of one typical experiment performed in duplicate and representative of three experiments which depicts hPRL transcriptional activity (% of activity vs. WT hPRL maximal effect referred as 100%) in presence of increasing concentrations (μg/ml) of: hPRL (—●—), Δ1-9-hPRL (—□—), Δ1-14-hPRL (—Δ—), Δ1-10-hPRL (——*——), Δ1-11-hPRL (——○——), Δ1-12-hPRL (——□——), Δ1-13-hPRL (——◇——).

Data of one typical experiment performed in duplicate and representative of three experiments are shown in FIG. 5 which depicts hPRL transcriptional activity (% of activity vs. WT hPRL maximal effect referred as 100%) in presence of increasing concentrations (µg/ml) of: hPRL (—●—), Δ1-9-hPRL (—□—), Δ1-14-hPRL (—Δ—), Δ1-10-hPRL (—*—), Δ1-11-hPRL (—○—), Δ1-12-hPRL (—□—), Δ1-13-hPRL (—◇—).

The results are expressed in fold induction of luciferase activity (i.e. percentage of activity vs WT hPRL maximal effect referred as 100%).

Analogs Δ1-9-hPRL, Δ1-10-hPRL, Δ1-11-hPRL, Δ1-12-hPRL and Δ1-13-hPRL were undistinguishable in this assay, with curves displaced to the left compared to WT hPRL ($EC_{50}$ decreased by ~2 fold). In addition, the maximal response induced by all these analogs was higher compared to WT hPRL (120-140%), reflecting super-agonistic properties.

In contrast, Δ1-14-hPRL was less active than hPRL, regarding both its dose-response curve ($EC_{50}$ ~3-fold higher) and its maximal activity (60% of WT hormone).

Antagonism

In agreement with their intrinsic agonistic activity, none of the N-terminal deletion mutants displayed antagonistic activity in any of the three bioassays used in this study (data not shown).

G129R Mutant and Double Mutants

All experiments involve the single mutant (G129R-hPRL) and the double mutants Δ1-9-G129R-hPRL and Δ1-14-G129R-hPRL.

Nb2 Cell Proliferation Assay

Figure 6:
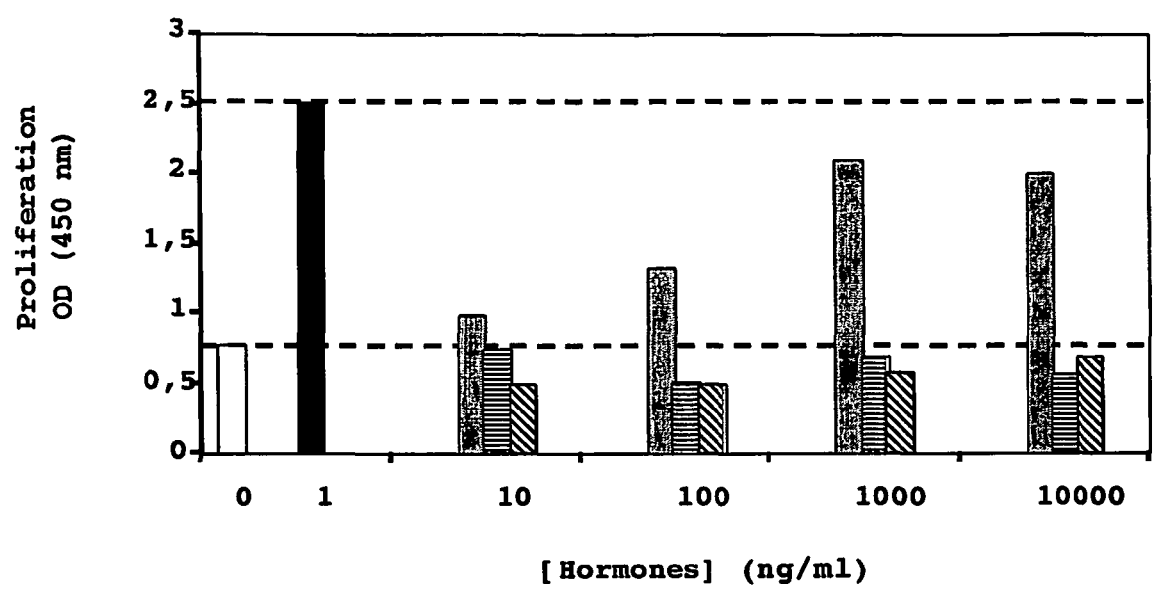
FIG. 6 shows agonism of G129R and double mutants by means of the Nb2 cell proliferation assay: cell proliferation without hPRL (□) and in presence of increasing concentrations of purified WT hPRL (■), G129R-hPRL Δ1-9-G129R-hPRL (▤) and Δ1-14-G129R-hPRL (▨).

AGONISM. FIG. 6 shows cell proliferation without hPRL (□) and in presence of increasing concentrations of purified WT hPRL (■), G129R-hPRL (□), Δ1-9-G129R-hPRL (▤) and Δ1-14-G129R-hPRL (▨)

WT hPRL induces maximal proliferation at 1-2 ng/ml, whereas the dose-dependent mitogenic effect of G129R-hPRL is shifted to the high concentrations, but reaches (sub) maximal proliferation. In contrast, both double N-Terminal deleted mutants Δ1-9-G129R-hPRL and Δ1-14-G129R-hPRL are devoid of significant agonistic activity.

As previously reported (GOFFIN et al., J. Biol. Chem., 269, 32598-32606, 1994; BERNICHTEIN et al., Endocrinology, 142, 3950-3963, 2001), the agonistic dose-response curve obtained with G129R-hPRL is shifted by more than two log units to the right compared to WT hPRL, with maximal effect achieved at about 0.5 to 1 µg/ml. Interestingly, this agonistic activity is totally abolished when N-terminal tail of G129R-hPRL is deleted (meaning in Δ1-9-G129R-hPRL and Δ1-14-G129R-hPRL analogs), and this was true even at concentrations up to 4 orders of magnitude higher than the concentration leading to maximal activity of WT hPRL (1 ng/ml vs 10 µg/ml).

Human PRLR Transcriptional Bioassay (HL5)

Figure 7:
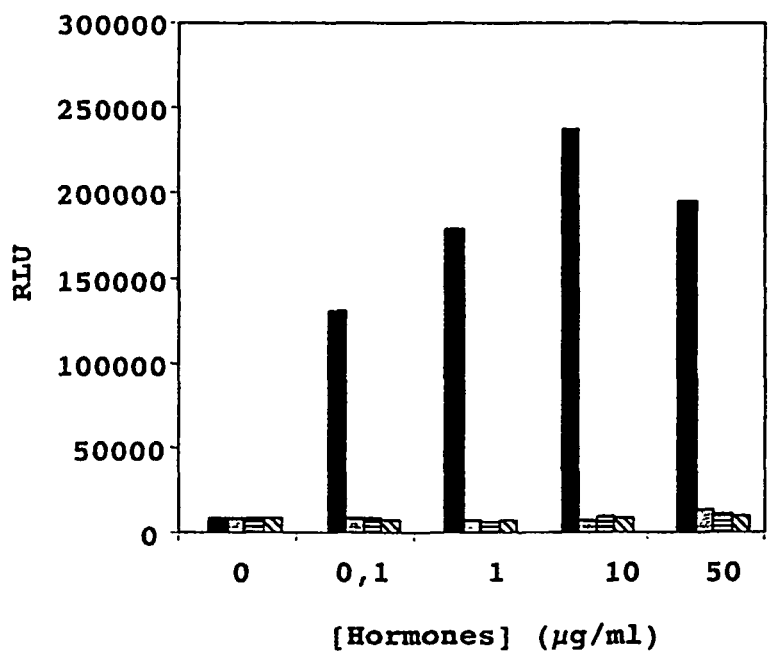
FIGS. 7A and 7B shown agonism and antagonism. 7A shows agonism by activation of the LHRE-luciferase reporter gene by increasing concentrations of WT hPRL (■), and the three G129R-containing analogs, G129R-hPRL G129R-hPRL (●), Δ1-9-G129R-hPRL (≡), and Δ1-14-G129R-hPRL (▤). The agonistic activity of G129R-hPRL is extremely reduced in this assay, reaching a maximal level <2% of hPRL activity. Similarly, none of the double mutant induced detectable level of luciferase activity, even when tested at extremely high concentrations (up to 50 μg/ml). The results demonstrating antagonism are shown in FIG. 7B: Δ1-14-G129R-hPRL(—■—), Δ1-9-G129R-hPRL (—▲—), G129R-hPRL (—◆—).
Figure 7:
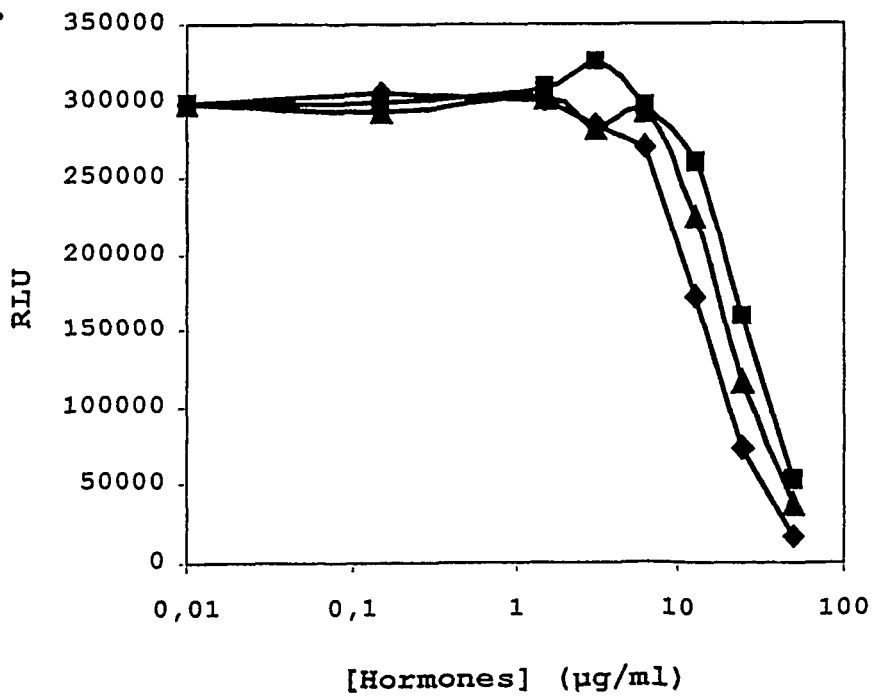

AGONISM. FIG. 7A shows activation of the LHRE-luciferase reporter gene by increasing concentrations of WT hPRL (■), and the three G129R-containing analogs, G129R-hPRL G129R-hPRL (□), Δ1-9-G129R-hPRL (▤), and Δ1-14-G129R-hPRL (▩).

The agonistic activity of G129R-hPRL is extremely reduced in this assay, reaching a maximal level <2% of hPRL activity. Similarly, none of the double mutant induced detectable level of luciferase activity, even when tested at extremely high concentrations (up to 50 μg/ml).

ANTAGONISM. The results are shown in FIG. 7B: Δ1-14-G129R-hPRL (—■—), Δ1-9-G129R-hPRL (—▲—), G129R-hPRL (—♦—).

In agreement with their relative affinity for the hPRLR, the antagonistic properties of the three analogs were very similar, but repeatedly showed the following order of activity: G129R-hPRL>Δ1-9-G129R-hPRL>Δ1-14-G129R-hPRL.

Ba/F3-hPRLR Cell Proliferation Bioassay

Figure 8:
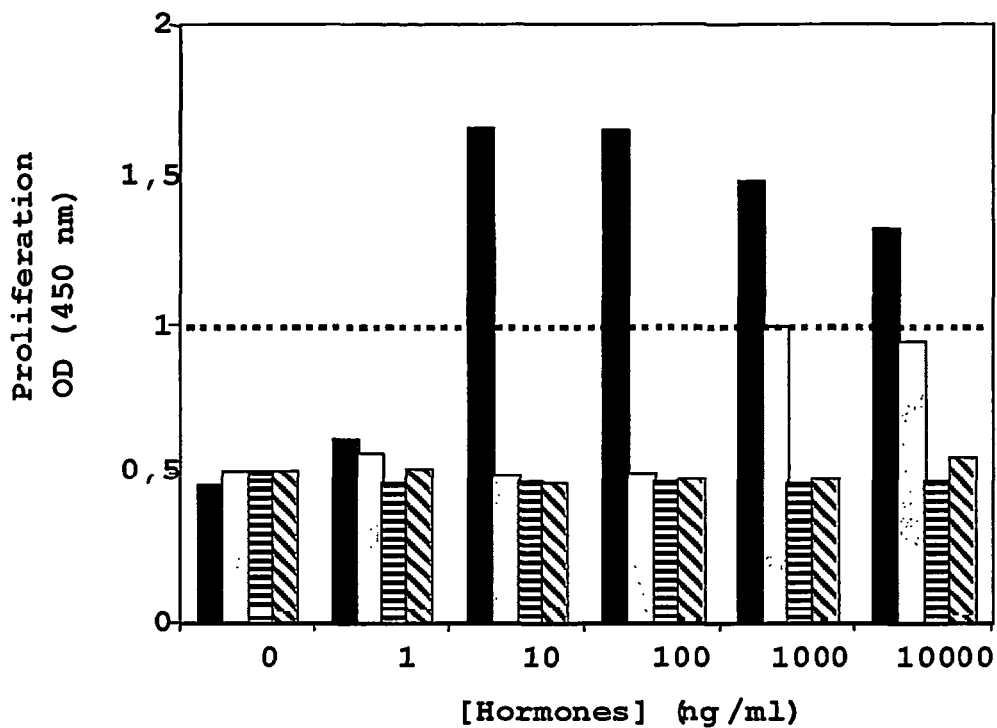
FIGS. 8A and 8B show agonism and antagonism using the Ba/F3-hPRLR cell proliferation bioassay.
Figure 8:
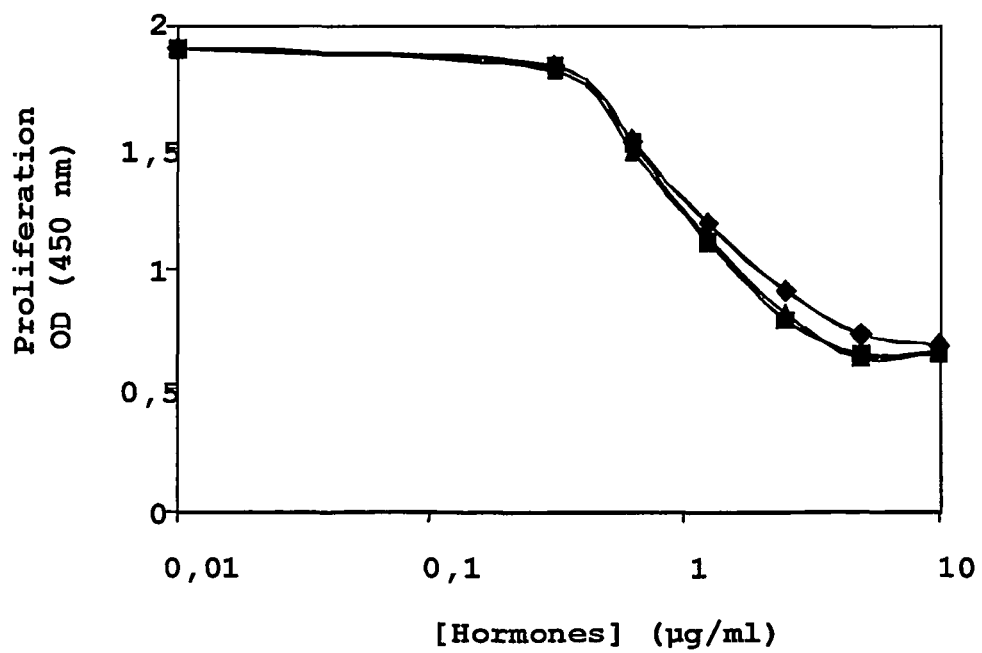

AGONISM. FIG. 8A shows cell proliferation in presence of increasing concentrations of purified WT hPRL (■), G129R-hPRL (□), Δ1-9-G129R-hPRL (▤), and Δ1-14-G129R-hPRL (▩).

Maximal effect of WT hPRL is obtained at 10 ng/ml. G129R-hPRL induced sub-maximal proliferation with a dose-response curve displaced by 2 logs to the high concentrations. In contrast, none of the double mutants (Δ1-9-G129R-hPRL and Δ1-14-G129R-hPRL) induced significant proliferation.

As in the Nb2 assay, the curve obtained for G129R-hPRL was displaced to the right by ~2 log units and achieved sub-maximal (50-80%) level compared to hPRL. At high concentrations, hPRL and G129R-hPRL displayed bell-shaped curves, a typical observation when using these ligands (KINET et al., Recent Res. Devel. Endocrinol., 2, 1-24, 2001). Both Δ1-9-G129R-hPRL and Δ1-14-G129R-hPRL failed to display any agonistic activity, even at concentration as high as 10 μg/ml.

ANTAGONISM. Antagonistic assays were performed by competing a fixed concentration of WT hPRL (10 ng/ml) with increasing concentrations of the analogs. FIG. 8B shows cell proliferation in presence of increasing concentrations of Δ1-9-G129R-hPRL (—■—), Δ1-14-G129R-hPRL (—▲—), G129R-hPRL (—♦—) competing with the fixed concentration of WT hPRL.

The three mutants in which Arg is substituted for Gly129 (G129R-hPRL, Δ1-9-G129R-hPRL and Δ1-14-G129R-hPRL) displayed similar antagonistic activities, meaning that efficient competition with WT hPRL required high molar excess of the analog being used (10 to 50 fold), irrespective of N-terminal deletions. With respect to the double mutants, the competitive inhibition of WT hPRL-induced activity presumably reflects a true phenomenon of antagonism, since these analogs are devoid of intrinsic agonistic effect (FIG. 8A). In contrast, since G129R-hPRL displays a significant agonistic activity, the inhibitory effect observed in competition assays presumably reflects a combination of real antagonism and self-antagonism phenomenon (GOFFIN et al., J. Biol. Chem., 269, 32598-32606, 1994; BERNICHTEIN et al., Endocrinology, 142, 3950-3963, 2001, KINET et al., Recent Res. Devel. Endocrinol., 2, 1-24, 2001).

EXAMPLE 4

Δ1-9-G129R Inhibits PRL-Induced MAPK Activation in Liver from Wild Type Balb-C/J Mouse Eight week old wild type balb-c/J females were treated with 10 μg hPRL or different ratios of hPRL versus antagonist (G129R-hPRL or Δ1-9-G129R-hPRL). Sixty minutes after intra-peritoneal (IP) injection of hormones, mice were sacrificed, their liver was rapidly harvested, dissected and homogenized, then cell lysates were prepared according to routine protocols. Seventy μg of lysates were loaded onto 10% SDS-PAGE, followed by liquid transfer onto nitrocellulose membranes. Membranes were blocked with 5% skimmed milk for 1 h at room temperature, and after extensive washing, they were incubated overnight with a primary monoclonal antibody specifically directed against the active forms of Erk1 and Erk2 MAP kinases (phosphorylated on threonine$^{202}$ and tyrosine$^{204}$) After extensive washing, membranes were incubated for 1 h with secondary horseradish peroxidase (HRP)-conjugated anti-mouse antibody. Immunoblots were revealed by enhanced chemiluminescence (ECL) followed by autoradiography.

Membranes were then dehybridized using stripping buffer for 30 min at 50° C., and after washing and reblocking, they were reprobed using the polyclonal anti-Erk1/Erk2 antibody which recognizes both active and inactive forms of Erk1 and Erk2 MAP kinases. Then, the blots were revealed after incubation with an HRP-conjugated anti-rabbit antibody.

Figure 9:
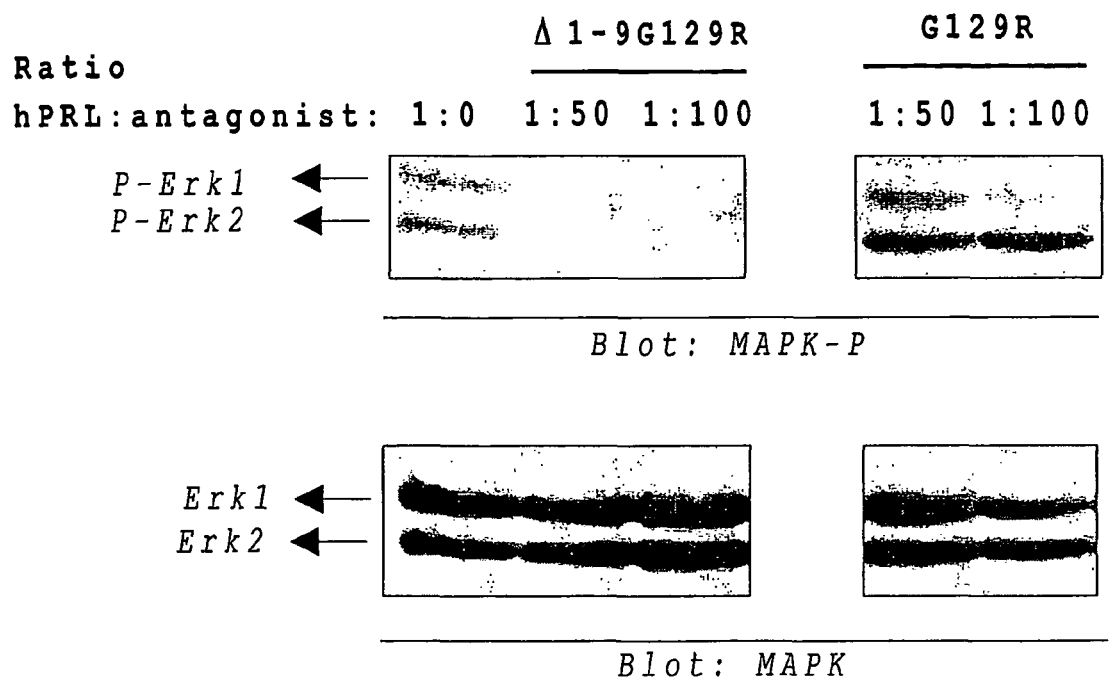
FIG. 9 depicts blots describing kinase activation describe by Example 4. A: anti-MAPK blots: top panel (MAPK-P): phosphorylated MAPK; bottom panel: total MAPK (MAPK). B: densitometric quantification of MAPK-P blots (top panels).
Figure 9:
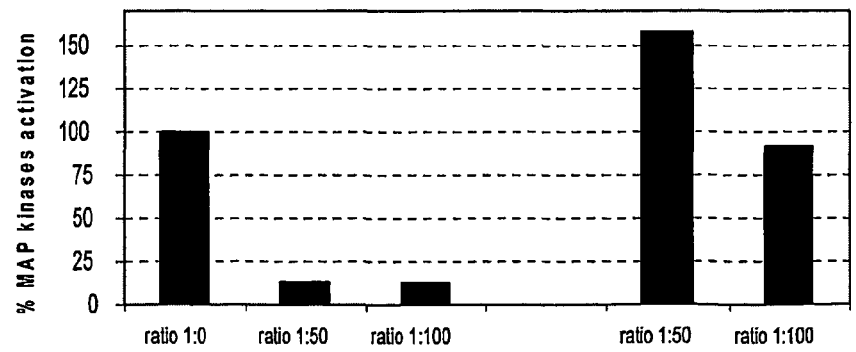

The results are shown in FIG. 9:

A: anti-MAPK blots:
top panel (MAPK-P): phosphorylated MAPK;
bottom panel: total MAPK (MAPK)
B: densitometric quantification of MAPK-P blots (top panels).

This experiment shows that MAP kinase activation induced by IP injection of 10 μg hPRL is inhibited by 50 fold molar excess of Δ1-9G129R-hPRL antagonist. In contrast, even at a higher molar ratio (100 fold), G129R-hPRL does not reduce MAPK activation and even appears to enhance it.

EXAMPLE 5

Δ1-9G129R Inhibits PRL-Induces STAT 3 and STAT 5 Activation in Lactating Mammary Gland from Wild Type Balb-C/J Mouse Antagonism.

Eight week old lactating (day 10 to 12) wild type balb-c/J female were treated (IP) with 200 μg bromocriptine to decrease circulating levels of endogenous PRL (bromocriptine is a dopamine-analog, the natural inhibitor of pituitary prolactin secretion). Five hours later, mice were treated (IP) for 30 min with 10 μg hPRL alone, or a 1:100 ratio of hPRL versus Δ1-9G129R-hPRL. Mice were then sacrificed; fourth mammary glands (right and left) were removed, pooled and homogenized according to routine protocols. Total cell lysates (2 mg) were used for immunoprecipitation (under overnight rotation at 4° C.) using polyclonal anti-STAT5 or polyclonal anti-STAT3 antibodies, respectively. Immunocomplexes were then captured with 20 μl Protein A Sepharose slurry by 1 h incubation under rotation. Protein A complexes were precipitated by centrifugation, pellets were washed, then boiled in reducing sample buffer for 5 min. Immunoprecipitated samples were analysed on 7.5% SDS-PAGE, followed by western-blotting as described in Example 4.

Primary antibodies (polyclonal) used in this experiment specifically recognize activated forms of Stat5 and Stat3 (anti-phosphorylated STAT5 and anti-phosphorylated STAT3, respectively). After dehybridization, membranes were reprobed using polyclonal antibodies recognizing total (phosphorylated and non phosphorylated form) Stat5 or Stat3.

Figure 10:
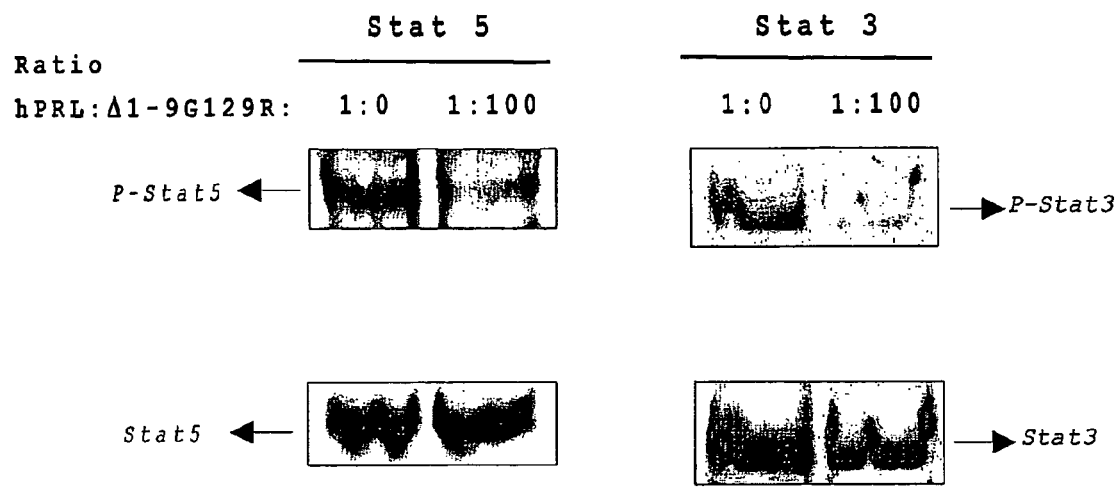
FIG. 10 shows Δ1-9G129R inhibition of PRL-induced Stat 3 and Stat 5 activation as shown by Example 5. A: anti-STAT blots: Top panel (P-Stat5 and P-Stat3): phosphorylated Stat5 and phosphorylated Stat3; Bottom panel (Stat5 and Stat3): total Stat5 and Stat3. B: densitometric quantification of anti-phosphorylated STAT blot (top panels).
Figure 10:
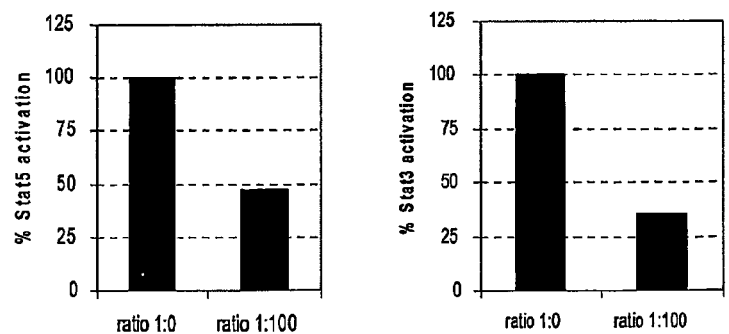

The results are shown in FIG. 10:

A: anti-STAT blots:

Top panel (P-Stat5 and P-Stat3): phosphorylated Stat5 and phosphorylated Stat3;

Bottom panel (Stat5 and Stat3): total Stat5 and Stat3.

B: densitometric quantification of anti-phosphorylated STAT blot (top panels).

The results show that activation of STAT3 and STAT5 by PRL in the lactating mammary gland is inhibited by addition of a 100 fold molar excess of Δ1-9G129R-hPRL.

EXAMPLE 6

Δ1-9-G129R Inhibits PRL-Induced MAPK Constitutive Activation in Prostates from Mice Transgenic for Human PRL, Rat PRL and G129R-Human PRL MAPK Activation Bioassay.

Agonists (PRL; G129R-hPRL)

This in vivo bioassay uses transgenic mice (males) expressing human PRL or G129R-hPRL under the control of the ubiquitous metallothionein promoter (Tg Met-hPRL and Tg Met-G129R), or expressing rat PRL under the control of the prostate-specific probasin promoter (Tg Prob-rPRL).

One year old transgenic males were sacrificed; uro-genital tractus was removed, and prostates were micro-dissected under microscope to separate ventral from dorsolateral lobes. Then, dorsolateral lobes were homogenized and cell lysates were prepared following routine protocols. Seventy μg of lysates were loaded onto 10% SDS-PAGE to test the spontaneous activation of Erk 1 and Erk 2 MAPK as described with liver in example 4.

Figure 11:
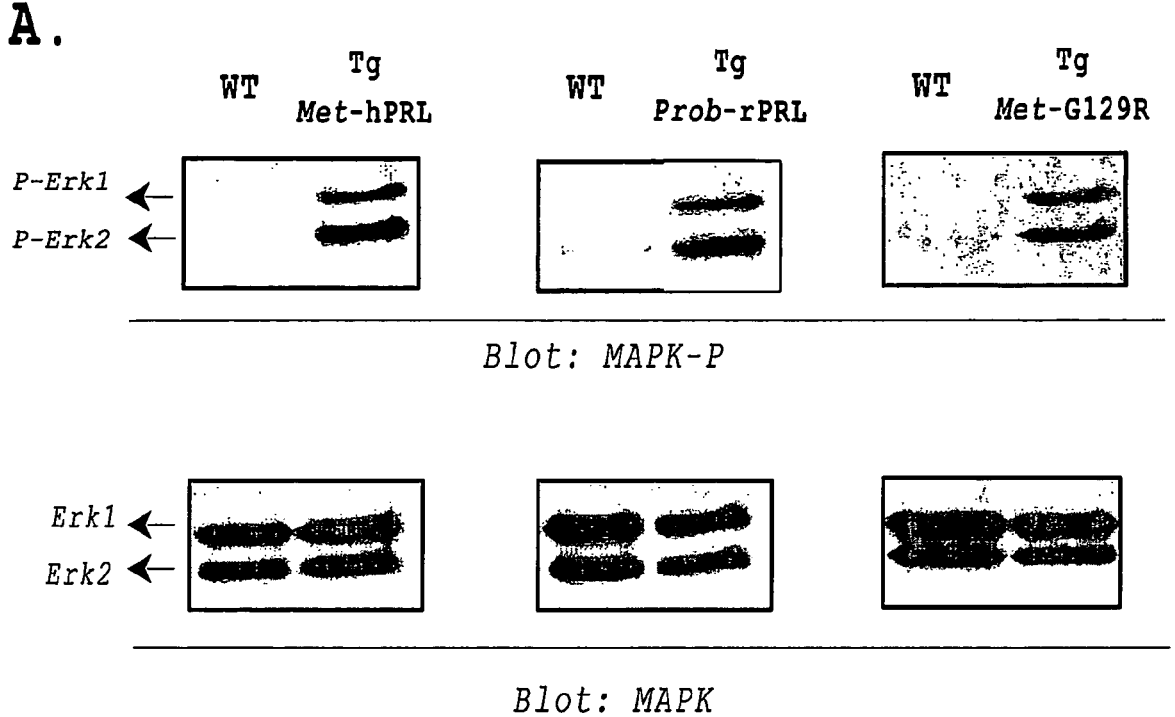
FIG. 11 shows that Δ1-9-G129R inhibits PRL-induced MAPK Constitutive activation as described in Example 6. A: anti-MAPK blots: Top panel (MAPK-P): phosphorylated MAPK; Bottom panel (MAPK): total MAPK. B: densitometric quantification of MAPK-P blots (top panels).
Figure 11:
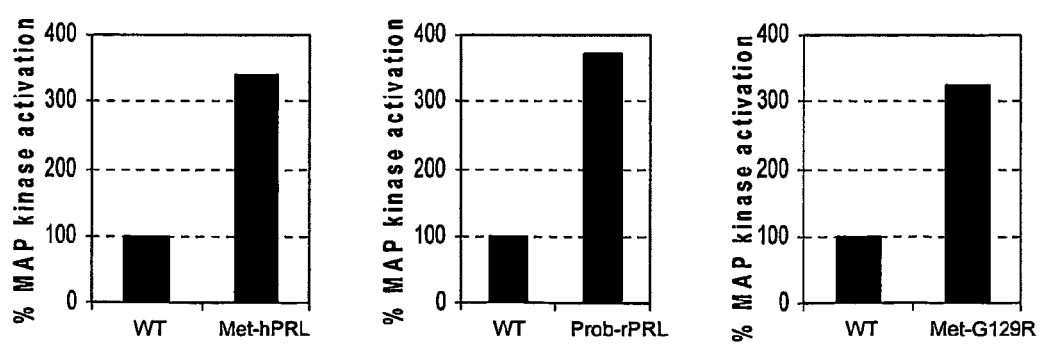

The result are shown in FIG. 11:

A: anti-MAPK blots:

Top panel (MAPK-P): phosphorylated MAPK;

Bottom panel (MAPK): total MAPK.

B: densitometric quantification of MAPK-P blots (top panels).

This experiment shows that MAP kinases are constitutively activated in the dorsolateral prostate lobes of all transgenic mouse lineages compared to non-transgenic littermates (WT). This indicates that local-production of PRL in the prostate leads to MAPK activation in this tissue.

Furthermore, FIG. 11 shows that G129R-hPRL displays an agonistic activity in vivo comparable to that of wild type prolactin.

Antagonist (Δ1-9G129R-hPRL)

Seven month old males from the transgenic mouse lineage expressing rat PRL under the control of prostate-specific probasin promoter were injected (IP) with 1 mg Δ1-9G129R-hPRL for 60 minutes. Mice were then sacrificed; uro-genital tractus was removed, and prostates were micro-dissected under microscope to separate ventral from dorsolateral lobes. Tissues were homogenized and cell lysates were prepared following routine protocols. Seventy μg of lysates were loaded onto 10% SDS-PAGE, followed by western-blotting as described in example 4.

Figure 12:
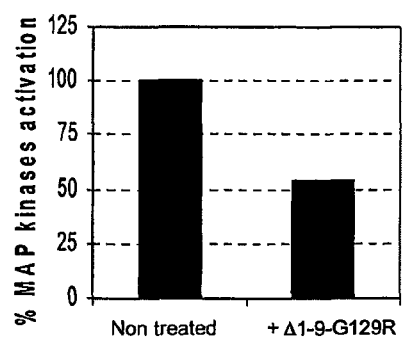
FIG. 12 refers to antagonist (Δ1-9G129R-hPRL) as also described in Example 6. A: anti-MAPK blots: Top panel (MAPK-P): phosphorylated MAPK in the prostate ventral and dorsolateral lobes and in the presence (+) or absence (−) of Δ1-9G129R-hPRL mutant.
Figure 12:
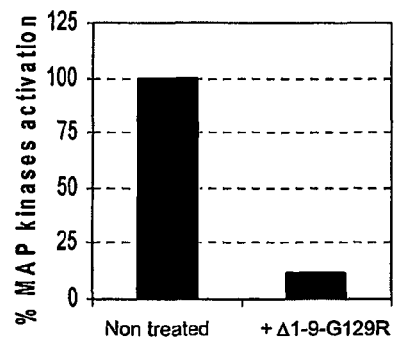

The results are shown in FIG. 12:

A: anti-MAPK blots:

Top panel (MAPK-P): phosphorylated MAPK in the prostate ventral and dorsolateral lobes and in the presence (+) or absence (−) of Δ1-9G129R-hPRL mutant;

Bottom panel (MAPK): total MAPK in the same samples.

B: densitometric quantification of anti-phosphorylated MAPK blot (top panels).

This experiment shows that the constitutive activation of MAP kinases by local expression of PRL in the prostate (autocrine-paracrine effect; see FIG. 11) is inhibited by injection of Δ1-9G129R-hPRL in both lobes.

The invention claimed is:

1. A variant of a wild-type mammalian prolactin wherein the variant is an antagonist of a mammalian prolactin receptor that exhibits no agonist activity on said receptor, said variant having:
   a) deletion of the first 9 to 14 N-terminal amino acids, and
   b) a sterically hindering mutation within binding site 2 of prolactin which is G129R;
   wherein said wild-type mammalian prolactin has cysteine residues at position 4 and position 11 of the mature prolactin, an alanine residue at position 22 of the mature prolactin, and a glycine residue at position 129 of the mature prolactin;
   wherein the above positions and numbered residues correspond to the amino acid sequence of human prolactin.

2. The variant of prolactin according to claim 1, wherein the 14 N-terminal residues of prolactin are deleted.

3. The variant of prolactin according to claim 1, wherein the 9 N-terminal residues of prolactin are deleted.

4. The variant of claim 1, which is a variant of human prolactin that has a human prolactin amino acid sequence except for said mutations.

5. An isolated polynucleotide encoding the prolactin variant of claim 1.

6. An expression cassette comprising the polynucleotide of claim 5.

7. A recombinant vector comprising the polynucleotide of claim 5.

8. An isolated host cell transformed by the polynucleotide of claim 5.

9. A method for treating a disease or disorder involving PRL-mediated effects comprising administering the prolactin variant of claim 1 to a subject in need thereof in an amount sufficient to antagonize the activity of prolactin.

* * * * *